United States Patent [19]

Shirley

[11] Patent Number: 5,511,543
[45] Date of Patent: Apr. 30, 1996

[54] DISPOSABLE RESUSCITATION DEVICE HAVING UNIDIRECTIONAL VALVE

[76] Inventor: Terry L. Shirley, 31471 Paseo Duran, San Juan Capistrano, Calif. 92675

[21] Appl. No.: 248,198

[22] Filed: May 24, 1994

Related U.S. Application Data

[63] Continuation of Ser. No. 931,712, Aug. 18, 1992, abandoned.

[51] Int. Cl.⁶ .................................................. A61M 16/00
[52] U.S. Cl. .................................. 128/203.11; 128/202.28
[58] Field of Search ...................... 128/202.28, 202.29, 128/203.11, 205.24

[56] References Cited

U.S. PATENT DOCUMENTS

| | | | |
|---|---|---|---|
| 4,819,627 | 4/1989 | Connors | 128/203.11 |
| 4,819,628 | 4/1989 | Eisenberg et al. | 128/203.11 |
| 4,858,605 | 8/1989 | Levy | 128/203.11 |
| 4,909,245 | 3/1990 | Wollenhaupt | 128/203.11 |
| 4,942,873 | 7/1990 | Irwin et al. | 128/203.11 |
| 4,953,831 | 9/1990 | Albrecht | 261/102 |
| 4,969,456 | 11/1990 | Cooper | 128/203.11 |
| 5,088,485 | 2/1992 | Schock | 128/203.11 |
| 5,119,809 | 6/1992 | Gerson | 128/203.11 |

Primary Examiner—Aaron J. Lewis
Attorney, Agent, or Firm—Stetina Brunda & Buyan

[57] ABSTRACT

A device for preventing disease transmission during manual rescue breathing has a flexible sheet configured to cover a victim's mouth and nose and a body disposed centrally within the flexible sheet. The body has a first tube insertible within a rescuer's mouth and a second tube in fluid communication with the first tube insertible within the victim's mouth such that the first and second tubes define a first airway through the body. A one-piece duckbill check valve is disposed within the body along the air path such that fluid communication is provided from the first tube to the second tube and is inhibited from the second tube to the first tube. Thus, while the rescuer can easily blow air through the body into the victim's mouth to inflate the victim's lungs, the victim is incapable of blowing air back through the body into the rescuer's mouth, thus potentially exposing the rescuer to contagious diseases. The duckbill valve is preferably molded of a flexible polymer material and is of integral construction to lower costs, simplify construction, and improve reliability. At least one exhaust aperture is formed in the body to define a second air path along which air is exhausted by the victim to ensure effective and efficient exhausting of the victim's lungs and thereby enhance the rescue breathing process. A valve member formed upon the duckbill valve closes the exhaust apertures when the rescuer blows into the first tube and permits the exhaust apertures to open when the victim exhausts air into the second tube.

3 Claims, 3 Drawing Sheets

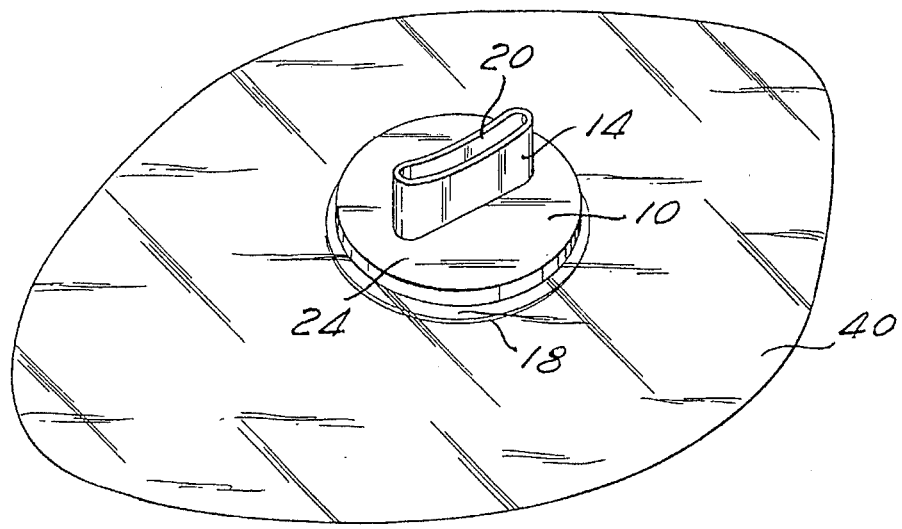
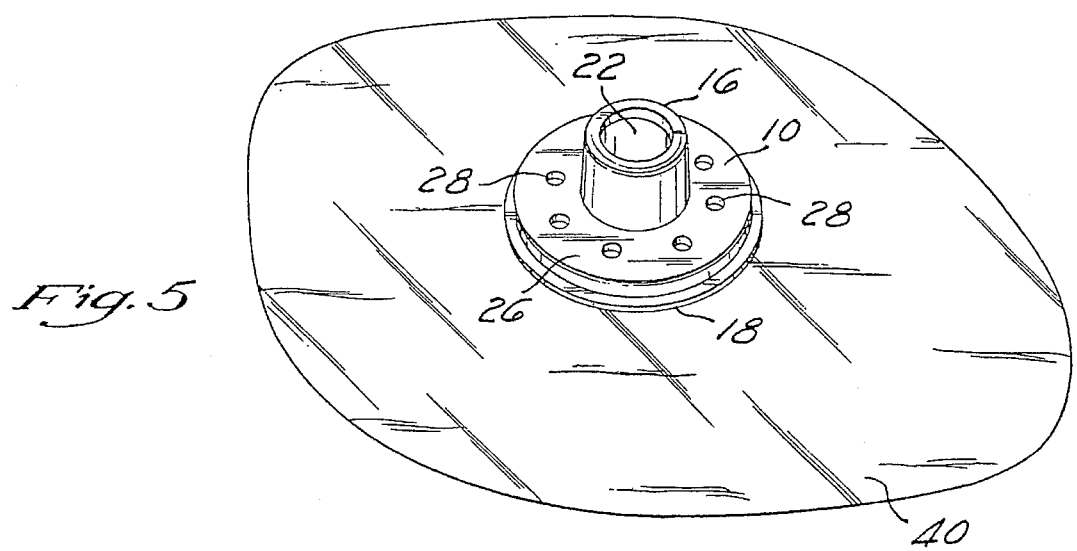
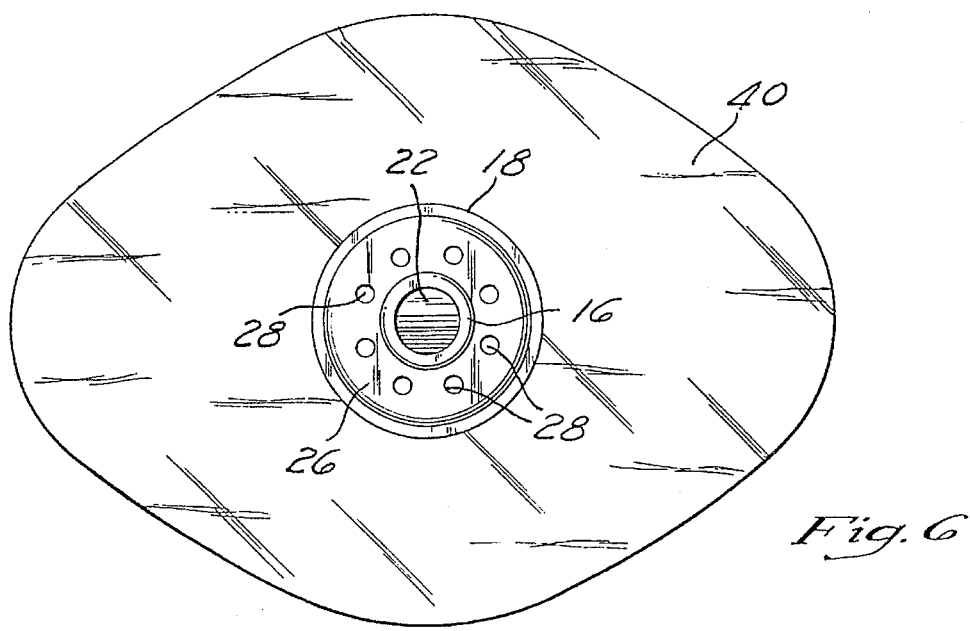

DISPOSABLE RESUSCITATION DEVICE HAVING UNIDIRECTIONAL VALVE

This application is a continuation of application Ser. No. 07/931,712, filed Aug. 18, 1992, now abandoned.

FIELD OF THE INVENTION

The present invention relates generally to medical devices and more particularly to a disposable resuscitation device having a unidirectional valve to prevent disease transmission during manual rescue breathing.

BACKGROUND OF THE INVENTION

Artificial resuscitation or rescue breathing is a first-aid technique for reviving a non-breathing victim. During rescue breathing, the rescuer blows air into a victim's mouth, thus inflating the victim's lungs and providing necessary oxygen thereto.

More specifically, the victim is placed upon his back, the mouth is opened, the airway checked for obstruction and cleared, and the head is tilted backward while the chin is pulled upward. The nostrils are then pinched closed and an air-tight seal is made with the lips of the rescuer to the victim's mouth such that air blown into the victim's mouth inflates the victim's lungs. Rescue breathing is continued until the rescuer is exhausted, another rescuer assumes rescue breathing, or the victim revives.

As can be appreciated, such intimate contact is generally thought to be associated with the risk of transmitting communicable diseases. Of particular concern is the transmission of such life-threatening diseases as AIDS and Hepatitis. In view of this, there is a tendency to avoid the mouth-to-mouth contact generally necessary for such artificial respiration or rescue breathing.

It is known to utilize various devices which have been devised to isolate or shield the rescuer's mouth from the victim during artificial resuscitation or rescue breathing. One example of such a device is described in U.S. Pat. No. 4,819,628, issued to Eisenberg et al., on Apr. 11, 1989, and entitled MOUTH-TO-MOUTH RESUSCITATION DEVICE.

The Eisenberg device utilizes a relatively complex one-way valve arrangement to isolate the rescuer from air exhausted from the victim's mouth. Such one-way valve is therefore relatively difficult to manufacture, costly, and subject to reliability problems. Furthermore, the Eisenberg device employs a plurality of grooves to facilitate exhalation by the victim. Such grooves do not provide an optimal pathway for the victim's exhaust breath and as such may actually inhibit breathing.

As such, although the prior art has recognized to a limited extent the problem of isolating a rescuer from a victim in order to mitigate the potential for disease transmission, the proposed solutions have to date been ineffective in providing a satisfactory remedy. It would be desirable to provide an improved device for preventing disease transmission during artificial resuscitation or manual rescue breathing wherein the one-way valve comprises a simple, inexpensive, and reliable construction, and provision is afforded for effective and efficient exhausting of the victim's lungs.

SUMMARY OF THE INVENTION

The present invention specifically addresses and alleviates the above-mentioned deficiencies associated in the prior art. More particularly, the present invention comprises a device for preventing disease transmission during manual rescue breathing and has a flexible sheet configured to cover a victim's mouth and nose.

A body is disposed centrally within the flexible sheet. The body has a first tube insertible within a rescuer's mouth and a second tube in fluid communication with the first tube insertible within the victim's mouth such that the first and second tubes define a first airway through the body. A one-piece duckbill check valve is disposed within the body along the air path such that fluid communication is provided from the first tube to the second tube and is inhibited from the second tube to the first tube.

Thus, while the rescuer can easily blow air through the body into the victim's mouth to inflate the victim's lungs, the victim is incapable of blowing air back through the body into the rescuer's mouth, thus potentially exposing the rescuer to contagious diseases. The duckbill valve is preferably molded of a flexible polymer material and is of integral construction to lower costs, simplify construction, and improve reliability.

At least one exhaust aperture is formed in the body to define a second air path along which air is exhausted by the victim to ensure effective and efficient exhausting of the victim's lungs and thereby enhance the rescue breathing process. A valve member formed upon the duckbill valve closes the exhaust apertures when the rescuer blows into the first tube and permits the exhaust apertures to open when the victim exhausts air into the second tube.

These, as well as other advantages of the present invention will be more apparent from the following description and drawings. It is understood that changes in the specific structure shown and described may be made within the scope of the claims without departing from the spirit of the invention.

BRIEF DESCRIPTION OF THE DRAWINGS

FIG. 4 is a perspective view showing the upper surface of the disposable resuscitator device of a second embodiment of the present invention;

FIG. 5 is a perspective view showing the lower surface of the disposable resuscitator device of a second embodiment of the present invention;

FIG. 6 is a top plan view of the lower surface of the disposable resuscitator device of FIGS. 4 and 5;

DETAILED DESCRIPTION OF THE PREFERRED EMBODIMENT

The detailed description set forth below in connection with the appended drawings is intended as a description of the presently preferred embodiments of the invention, and is not intended to represent the only forms in which the invention may be constructed or utilized. The description sets forth the functions and sequence of steps for constructing and operating the invention in connection with the illustrated embodiments. It is to be understood, however, that the same or equivalent functions and sequences may be accomplished by different embodiments that are also intended to be encompassed within the spirit and scope of the invention.

Figure 1:
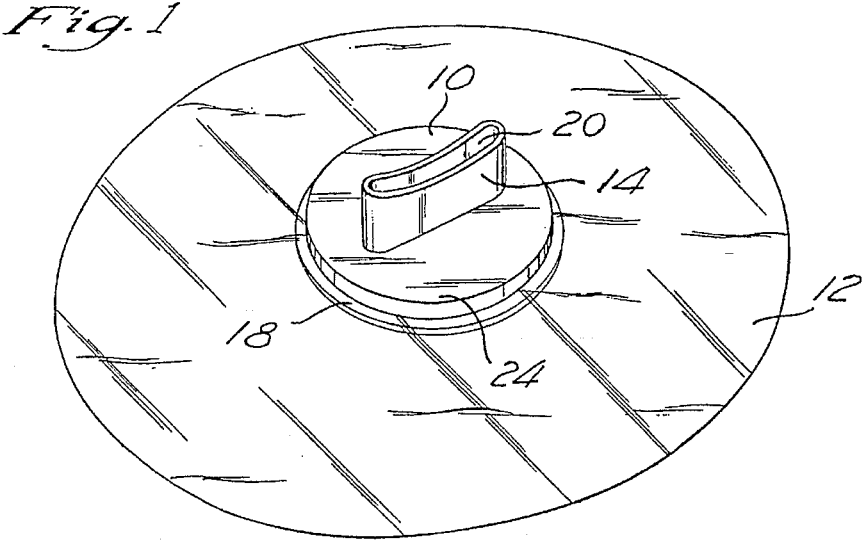
FIG. 1 is a perspective view showing the upper surface of the disposable resuscitator device of a first embodiment of the present invention.
Figure 2:
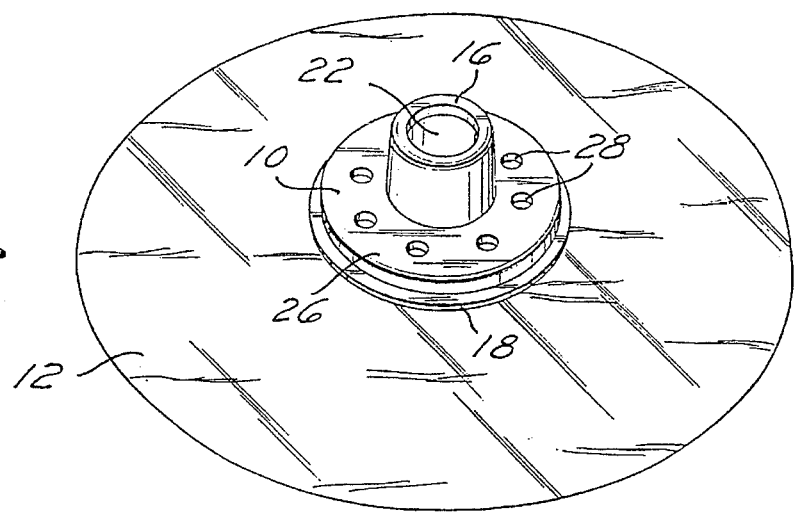
FIG. 2 is a perspective view showing the lower surface of the disposable resuscitator device of a first embodiment of the present invention.
Figure 3:
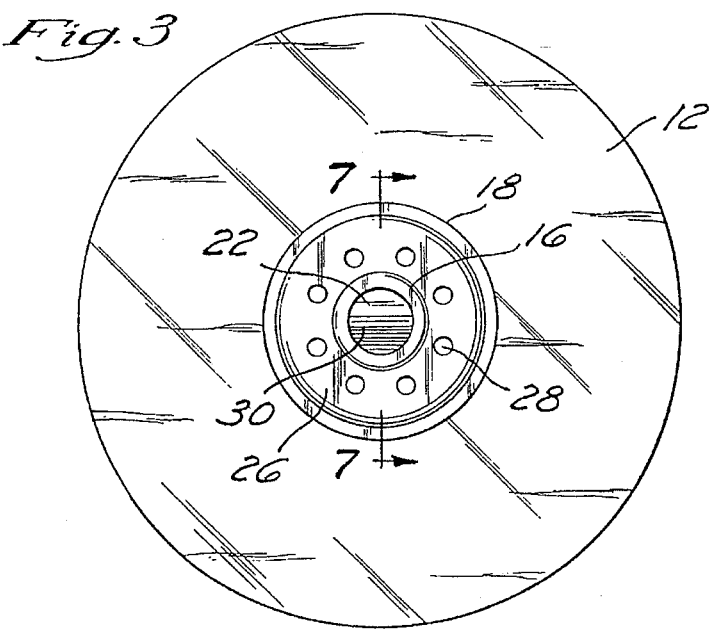
FIG. 3 is a top plan view of the lower surface of the disposable resuscitator device of FIGS. 1 and 2.

The disposable resuscitator device of the present invention is illustrated in FIGS. 1–8 which depict two presently preferred embodiments of the invention. Referring now to FIGS. 1–3, the disposable resuscitator is generally comprised of a body 10 having a generally circular flexible sheet 12 extending from the periphery therefrom. The flexible sheet 12 is configured to cover a victim's mouth and nose and thereby isolate the rescuer therefrom while simultaneously providing a substantially air-tight seal. The body 10 is preferably disposed at approximately the center of the substantially circular flexible sheet 12.

Figure 7:
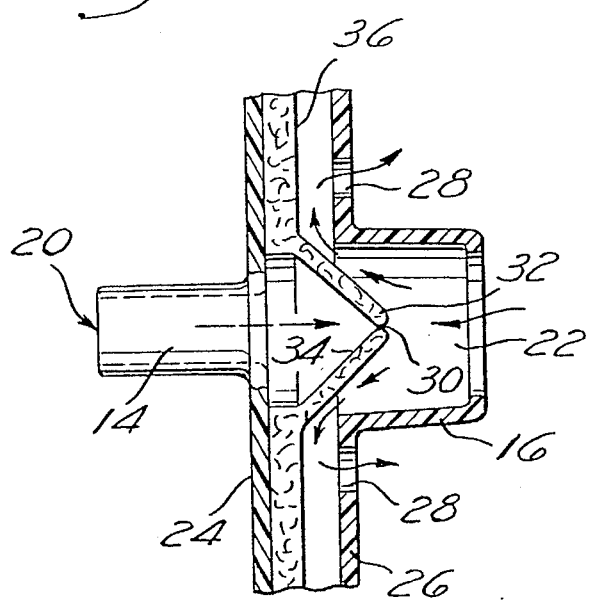
FIG. 7 is a cross-sectional side view of the body of the disposable resuscitator device of FIGS. 1–6 illustrating the duckbill valve in the closed position and showing the victim's exhaust air path.
Figure 8:
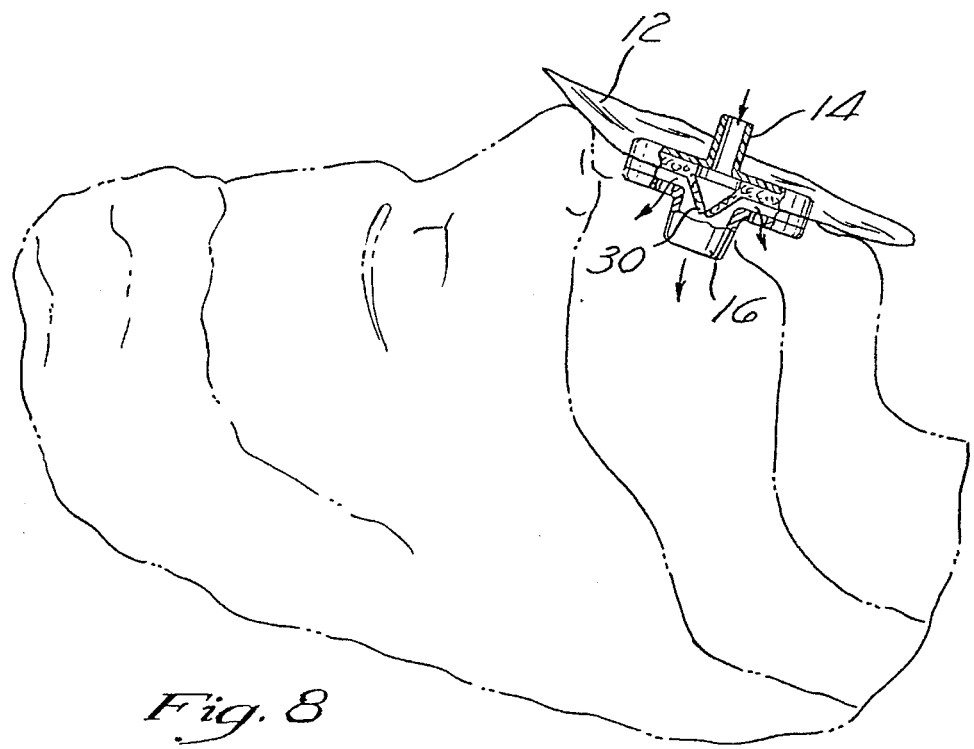
FIG. 8 is a cross-sectional side view of the disposable resuscitator device positioned for use within a victim's mouth and showing the duckbill valve in an opened configuration.

Referring now to FIGS. 7 and 8, the body 10 has a generally oval first tube 14 extending upwardly from the upper surface 24 thereof and having a bore 20 formed therein. A circular second tube 16 extends downwardly form the lower surface 26 of the body 10 and similarly has a bore 22 formed therein. The bore 22 of the second tube 16 is in fluid communication with the bore 20 of the first tube 14 such that a rescuer may blow air therethrough to effect inflation of the victim's lungs.

A plurality of exhaust apertures 28 facilitate exhausting of the victim's lungs when the victim exhales and forces air into the bore 22 of the second tube 16. A duckbill check valve 30 is disposed within the body 10 such that air blown into the first tube 14 is communicated therethrough and into the second tube 16. Blowing air into the first tube 14 causes the first 32 and second 34 valve members to separate (as best shown in FIG. 8), thereby allowing the passage of air therethrough.

Conversely, the blowing of air into the second tube 16 forces the first 32 and second 34 valve members tightly together, thus blocking the passage of air through the duckbill check valve 30.

An exhaust valve member 36 is formed about the duckbill check valve 30 such that blowing into the first tube 14 urges the duckbill check valve 30 and the exhaust valve member 36 toward the second tube 16, thus permitting the exhaust valve member 36 to block the exhaust apertures 28 and thereby only allow the air blown into the first tube 14 to exit through the second tube 16 and then enter the victim's lungs. Exhalation of the victim causes the duckbill valve 30 and the exhaust valve member 36 to move toward the first tube 14, thus opening the exhaust apertures 28 and allowing the victim's exhaled air to exit therethrough.

Referring now to FIGS. 4–6, a second embodiment of the disposable resuscitator device of the present invention is illustrated. In the second embodiment, the flexible sheet is configured in a generally elliptical or oval shape to better facilitate covering of the victim's mouth and nose. It must be appreciated that an air-tight seal is required in order to facilitate effective and efficient inflation of the victim's lungs during artificial resuscitation or rescue breathing. As such, it is necessary to adequately cover and seal the region immediately adjacent the victim's mouth as well as the victim's nostrils. Such covering and sealing is best effected by an elongate flexible sheet configuration wherein the sheet extends substantially over the victim's nose.

In both embodiments of the present invention the body is preferably comprised of a molded rigid plastic material, such as polyvinyl chloride, and the sheet is preferably comprised of a molded flexible plastic material, such as vinyl.

Having described the structure of the disposable resuscitator device of the present invention, it may be beneficial to describe the operation thereof. To use the disposable resuscitator device of the present invention, a non-breathing victim is first rolled gently onto his back, being careful to pull on both the hip and shoulder simultaneously to avoid the aggravation of any potential spinal injuries. After verifying that the victim is not breathing, the airway is checked for obstruction and cleared if necessary. The head is then tilted and the chin lifted to insure a clear airway, i.e. that the tongue is out of the way and a substantially straight path is provided through the trachea.

The second tube is inserted into the victim's mouth and the flexible sheet is held in place over the victim's nose and around the victim's mouth, such that a substantially air-tight seal is formed thereby. In the second embodiment of the present invention, an elongate portion of the flexible sheet is positioned over the victim's nose to assure optimal sealing. CPR is commenced by blowing into the first tube 14 to inflate the victim's lungs.

Blowing into the first tube 14 by the rescuer forces the exhaust valve member 36 and duckbill check valve 30 toward the second tube 16, thus covering the exhaust apertures 28 with the exhaust valve member 36, and additionally forces the first 32 and second 34 valve members to separate such that the air blown into the first tube 20 travels through the duckbill valve 30 and second tube 16 and thus effects inflation of the victim's lungs.

Exhalation by the victim causes air to enter the second tube 16 and thus force the exhaust valve member toward the first tube 14, thereby opening the exhaust apertures 28. Air flow into the second tube 16 forces the first 32 and second 34 valve members together such that air flow to the first tube 14 is prevented. The air exhausted by the victim is thus forced to flow through the exhaust apertures 28, rather than through the first tube 14, thereby isolating the rescuer therefrom.

It is understood that the exemplary disposable resuscitation devices described herein and shown in the drawings represent only presently preferred embodiments of the invention. Indeed various modifications and additions may be made to such embodiments without departing from the spirit and scope of the invention. For example, various shapes and configurations of the first 14 and second 16 tubes are contemplated. Also, various shapes and configurations of the body 10 are likewise suitable. For example, the body 10 may be generally square, rectangular, octagonal, etc., in shape and still function as intended. Thus, these and other modifications and additions may be obvious to those skilled in the art and may be implemented to adapt the present invention in a variety of different applications.

What is claimed is:

1. A device for preventing disease transmission during manual rescue breathing, said device comprising:

(a) a flexible sheet configured to cover a victim's mouth and nose;

(b) a body disposed substantially centrally within said flexible sheet, said body comprising:

(i) a first tube insertable into a rescuer's mouth;

(ii) a second tube in fluid communication with said first tube and insertable into a victim's mouth, said first and second tubes defining a first air path through said body;

(c) at least one aperture formed in said body, said aperture(s) between said flexible sheet and said second tube, said aperture(s) defining a second air path through which air exhausted by a victim exits said body between said flexible sheet and said second tube for preventing the exhausted air from being directed toward a rescuer, wherein said aperture(s) formed in said body allows a victim to exhale through a victim's mouth and means for closing said aperture(s) formed in said body when air is blown into said first tube.

2. The device as recited in claim 1 further comprising a one-piece duckbill check valve disposed within said body along said air path such that fluid communication is provided from said first tube to said second tube and is inhibited from said second tube to said first tube.

3. The device as recited in claim 2 wherein said means for closing said aperture(s) comprises an exhaust valve member formed upon said duckbill valve such that blowing into said first tube causes said valve member to close said apertures and blowing into said second tube causes said valve member to open said aperture(s).

\* \* \* \* \*